(12) United States Patent
Lee et al.

(10) Patent No.: US 10,350,029 B2
(45) Date of Patent: Jul. 16, 2019

(54) VIBRATOR FOR ATTACHING COMPOSITE RESIN TO A TOOTH

(71) Applicant: B&L BIOTECH, INC., Ansan-si, Gyeonggi-do (KR)

(72) Inventors: In Whan Lee, Seoul (KR); Dong Yoon Lee, Seoul (KR); Seung Ki Baek, Seoul (KR); Gil Hwan Sung, Seoul (KR); In Jeong Choi, Seoul (KR); Myun Hwan Ahn, Namyangju-si (KR)

(73) Assignee: B&L BIOTECH, INC., Ansan-si (KR)

( * ) Notice: Subject to any disclaimer, the term of this patent is extended or adjusted under 35 U.S.C. 154(b) by 0 days.

(21) Appl. No.: 15/423,722

(22) Filed: Feb. 3, 2017

(65) Prior Publication Data

US 2017/0245959 A1  Aug. 31, 2017

(30) Foreign Application Priority Data

Feb. 26, 2016 (KR) .......................... 10-2016-0023626

(51) Int. Cl.
*A61C 3/08* (2006.01)
*A61C 5/60* (2017.01)
*A61C 1/07* (2006.01)
*A61C 1/00* (2006.01)

(52) U.S. Cl.
CPC .............. *A61C 3/08* (2013.01); *A61C 1/0015* (2013.01); *A61C 1/07* (2013.01); *A61C 5/60* (2017.02)

(58) Field of Classification Search
CPC .... A61C 3/00; A61C 3/19; A61C 3/08; A61C 5/60; A61C 1/0015; A61C 1/07; A61C 1/0007; A61C 1/02

USPC ..... 433/86, 99, 27, 226, 118, 119, 120, 127; 606/169, 170, 174, 39, 166, 167, 168; 604/22; 128/751, 755
See application file for complete search history.

(56) References Cited

U.S. PATENT DOCUMENTS 5,133,661 A   7/1992  Euvrard
6,086,369 A *  7/2000  Sharp .................... A61C 17/20
                                              433/118

(Continued)

FOREIGN PATENT DOCUMENTS

JP       2005-334024 A    12/2005
JP           3172877 B2     6/2011
KR    10-2011-0115645 A    10/2011

OTHER PUBLICATIONS

Communication issued Jan. 26, 2017 by the Korean Patent Office in a counterpart Korean Patent Application No. 10-2016-0023626.

*Primary Examiner* — Heidi M Eide
*Assistant Examiner* — Mirayda A Aponte
(74) *Attorney, Agent, or Firm* — Sughrue Mion, PLLC

(57) ABSTRACT

A vibrator for attaching composite resin to a tooth includes a housing, a vibration motor accommodated in the housing and configured to generate vibration, a micro-computer configured to control an operation and a vibration frequency of the vibration motor, a vibration tip configured to couple with one side of the housing to be exposed to an outside of the housing and to transfer the vibration to the composite resin, a vibration bushing provided at one end of the vibration tip and accommodated in the housing, and a control switch provided on one side of the housing and configured to generate a vibration motor control signal in response to a user contacting or pushing the control switch.

2 Claims, 1 Drawing Sheet

(56) References Cited

U.S. PATENT DOCUMENTS

| | | | |
|---|---|---|---|
| 7,959,438 B2* | 6/2011 | Feine | A61C 17/20 |
| | | | 310/17 |
| 2006/0234185 A1 | 10/2006 | Ziemba | |
| 2010/0003636 A1* | 1/2010 | Wagner | A61C 5/62 |
| | | | 433/89 |
| 2011/0143303 A1* | 6/2011 | Kilcher | A61C 1/07 |
| | | | 433/27 |

* cited by examiner

VIBRATOR FOR ATTACHING COMPOSITE RESIN TO A TOOTH

CROSS-REFERENCE TO RELATED APPLICATION

This application claims the priority benefit of Korean Patent Application No. 10-2016-0023626 filed on Feb. 26, 2016, in the Korean Intellectual Property Office, the disclosure of which is incorporated herein by reference.

BACKGROUND

1. Field of the Invention

At least one example embodiment relates to a device for attaching composite resin to a tooth, and more particularly, to a vibrator for attaching composite resin to a vertex of a tooth using vibration energy.

2. Related Art

A variety of procedures have been conducted for the purposes of treatment, beauty, and the like, in the field of dental treatment. To this end, various types of instruments have been developed and used.

Composite resin has a light transmittance similar to that of natural teeth and various chroma. Also, the composite resin is a material for removing organic substances, such as food residues, etc., by acid etching processing on dentin and/or enamel of a tooth and then filling the tooth using adhesiveness. For such tooth filling, an instrument is used to form a dental vertex and to attach the composite resin to the vortex.

In detail, once a vortex groove is formed on a tooth through a vortex, composite resin is applied to an inlet in which a tubule is formed to fill or close the tubule formed on dentin or enamel. Here, before applying the composite resin, a bonding agent may be applied. In the case of attaching the composite resin to the tooth after performing acid etching processing, the composite resin may be iteratively applied as a plurality of layers to prohibit generation of space or bubbles in the composite resin. The composite resin may be classified into a flowable type that is formed using liquid or a type similar to the liquid and also allows flow, and a non-flowable type that does not allow flow. The composite resin is mixed in a separate container and scooped through a tool, and then applied to the tooth. The tool is generally formed using a metal material, such as stainless steel and the like.

Here, when applying the composite resin to the tooth through the tool and then removing the tool, a portion of the composite resin may adhere to the tool whereby space or bubbles may be formed between layers of the composite resin. That is, a portion of the composite resin may come out in a direction in which the tool is detached from the tooth. Accordingly, minute bubbles may be generated between the composite resin and the dentin or enamel of the tooth and coupling between both becomes unstable.

Also, during a process of applying the composite resin as the plurality of layers, bubbles may be formed therein and not be removed. Once applying of the composite resin is completed, the composite resin is hardened through photopolymerization reaction by emitting light.

If treatment is completed without bubbles, etc., being removed, a patient may have a dull pain. In a serious case, the composite resin may be separate from the tooth.

Korean Patent Publication No. 10-2011-0115645 discloses a device and method for providing composite resin on a tooth.

SUMMARY

The present disclosure is conceived to provide a further detail and realistic vibrator for attaching composite resin to a tooth, and at least one example embodiment provides a vibrator that may effectively transfer vibration to a vibration tip and may remove bubbles and space formed in composite resin.

According to an aspect of at least one example embodiment, there is provided a vibrator for attaching composite resin to a tooth, the vibrator including a housing; a vibration motor accommodated in the housing and configured to generate vibration; a micro-computer configured to control an operation and a vibration frequency of the vibration motor; and a vibration tip configured to couple with one side of the housing to be exposed to an outside of the housing, and to transfer the vibration to the composite resin.

The vibrator may further include a control switch provided on one side of the housing and configured to generate a vibration motor control signal in response to a manipulation of a user. The vibration frequency of the vibration motor may vary based on whether the vibration motor control signal is generated and a number of generations of the vibration motor control signal.

The vibration frequency of the vibration motor may increase according to an accumulation of a generation of the vibration motor control signal within a preset generation count range of the vibration motor control signal.

The vibrator may further include a vibration bushing provided at one end of the vibration tip and accommodated in the housing. The vibration bushing may be configured to decrease a vibration frequency of the vibration tip by adding a mass to the vibration tip.

The vibration bushing may be separate from the vibration motor by a preset distance. The vibrator may further include a vibration tip rotation handler provided between the vibration tip and the vibration bushing and configured to rotate the vibration tip. A user rotates the vibration tip to a desired location through the vibration tip rotation handler.

According to example embodiments, it is possible to remove bubbles and space formed in composite resin by effectively transferring vibration to a vibration tip.

Other features and aspects will be apparent from the following detailed description, the drawings, and the claims.

BRIEF DESCRIPTION OF THE DRAWINGS

These and/or other aspects, features, and advantages of the invention will become apparent and more readily appreciated from the following description of embodiments, taken in conjunction with the accompanying drawings of which.

DETAILED DESCRIPTION OF THE INVENTION

Figure 1:
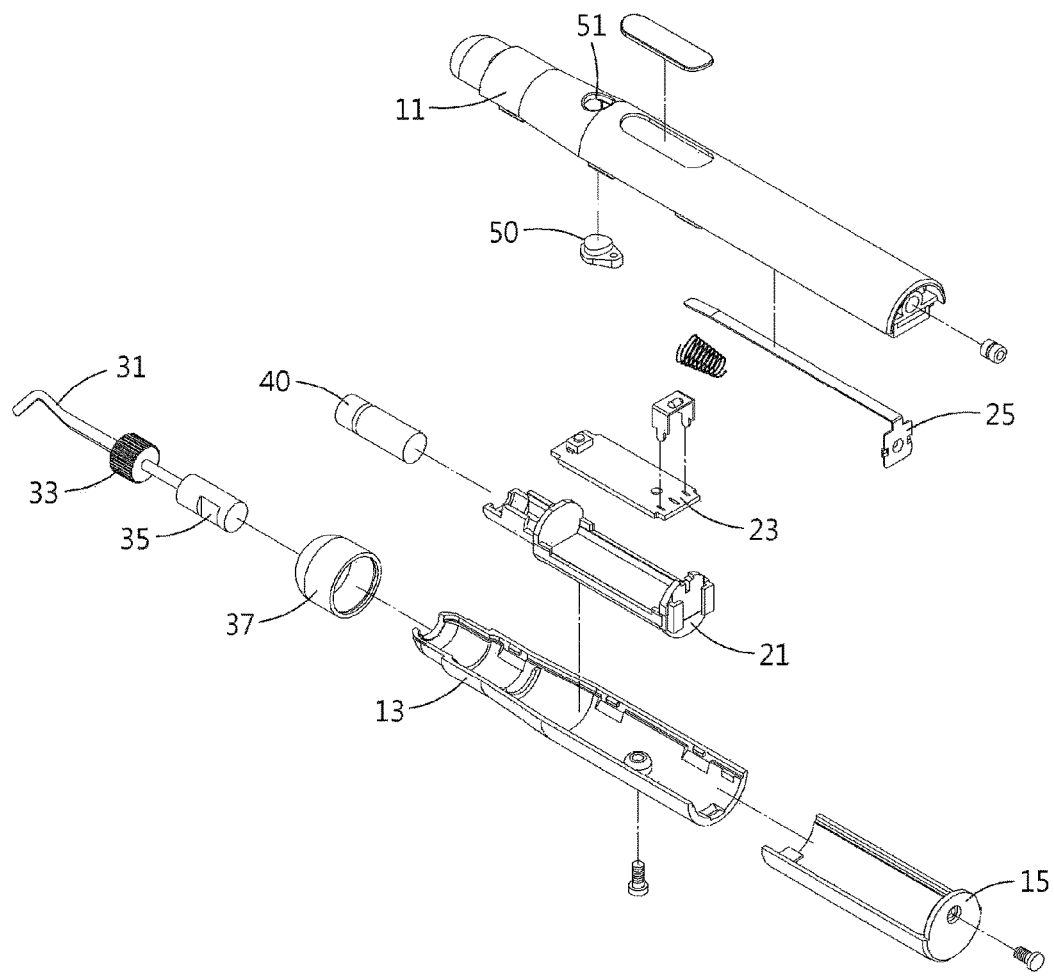
FIG. 1 is an exploded perspective view of a vibrator for attaching composite resin to a tooth according to an example embodiment.

Hereinafter, example embodiments will be described with reference to the accompanying drawings. Herein, thicknesses of lines, sizes of constituent elements, etc., illustrated in the drawings, may be exaggerated for clarity and convenience of description. Further, terms described in the following are ones defined based on functions in the present disclosure and thus, may vary based on the intent of a user or an operator, or custom. Accordingly, the definition of such terms should be made based on the overall description disclosed in the present specification.

Although the terms "first," "second," "third," etc., may be used herein to describe various elements, components, regions, layers, and/or sections, these elements, components, regions, layers, and/or sections, should not be limited by these terms. These terms are only used to distinguish one element, component, region, layer, or section, from another region, layer, or section. Thus, a first element, component, region, layer, or section, discussed below may be termed a second element, component, region, layer, or section, without departing from the scope of this disclosure.

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

Hereinafter, example embodiments will be described with reference to the accompanying drawings.

Figure 2:
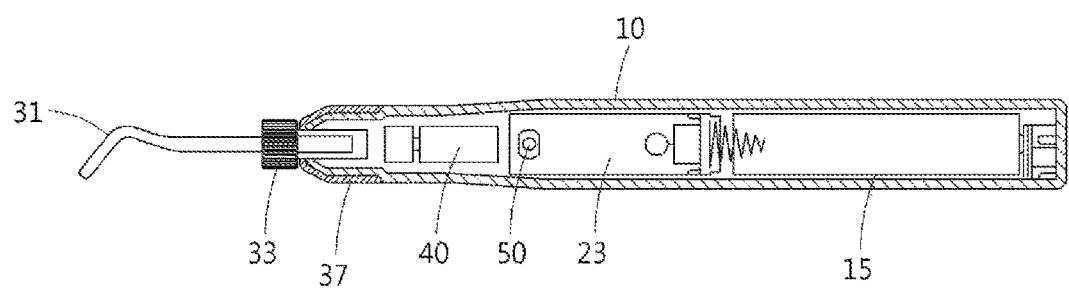
FIG. 2 is a cross-sectional view of a vibrator for attaching composite resin to a tooth according to an example embodiment.

FIG. 1 is an exploded perspective view of a vibrator for attaching composite resin to a tooth according to an example embodiment, and FIG. 2 is a cross-sectional view of a vibrator for attaching composite resin to a tooth according to an example embodiment.

Referring to FIGS. 1 and 2, the vibrator may include a housing 10 including an upper housing 11 and a lower housing 13. Also, the vibrator may include a vibration motor 40 accommodated in the housing 10 and configured to generate vibration. Also, the vibrator may include a micro-computer 23 configured to control an operation and a vibration frequency of the vibration motor 40. Also, the vibrator may include a vibration tip 31 configured to couple with one side of the housing 10 to be exposed to an outside of the housing 10, and to transfer the vibration to the composite resin.

The housing 10 may include the upper housing 11 and the lower housing 13. Space in which the vibration motor 40 and the micro-computer 23 are accommodated is formed through coupling of the upper housing 11 and the lower housing 13. The housing 10 may be configured in various shapes and may be configured to have a circular cross-section to be easily gripped by a user.

The upper housing 11 and the lower housing 13 may be coupled with each other through a housing coupler 37.

The vibration motor 40 is provided in the housing 10 to generate the vibration. The vibration motor 40 is received and thereby accommodated in the housing 10. Any type of motors capable of generating vibration may be used for the vibration motor 40. Herein, the vibration motor 40 may be, for example, an eccentric rotation motor. However, it is provided as an example only and a linear vibration motor may be employed for the vibration motor 40.

The vibration motor 40 is supplied with power from an outside and operates with the supplied power. Although not illustrated, the vibrator motor 40 may be supplied with power from a battery provided to one side of the housing 10 in order to enhance the portability of the vibrator. However, without being limited thereto, the vibration motor 40 may be supplied with power from an outside through a power line connected thereto.

The battery may be accommodated in a battery receiver 15 provided to one side of the housing 10. The power of the battery may be transferred to the micro-computer 23 and the vibration motor 40 through a power terminal 25.

The micro-computer 23 controls the operation and the vibration frequency of the vibration motor 40. The micro-computer 23 may be fixably mounted to a micro-computer holder 21 provided in the housing 10. The micro-computer 23 may control a rotary speed or the vibration frequency of the vibration motor 40 through pulse width modulation (PWM) control. In addition, the micro-computer 23 may increase, or alternatively, maximize a battery lifespan using a low power consumption typed power integrated circuit (IC).

The vibration tip 31 is coupled with one side of the housing 10, exposed to an outside of the housing 10, and transfers the vibration to the composite resin. The vibration generated at the vibration motor 40 is transferred to the vibration tip 31. The vibration tip 31 transfers the vibration to the composite resin in contact with the composite resin.

An end of the vibration tip 31 may be curved to easily make a contact with the composite resin.

The vibration tip 31 vibrates in contact with the composite resin and removes bubbles formed in the composite resin or space formed between layers of the composite resin.

Meanwhile, according to an example embodiment, the vibrator may further include a control switch 50 provided on one side of the housing 10 and configured to generate a vibration motor control signal in response to a manipulation of a user.

The control switch 50 may be inserted into a switch hole 51 formed on the housing 10, particularly, the upper housing 11, and may be exposed to an outside of the housing 10.

The user may control the operation of the vibration motor 40 by manipulating the control switch 50.

The control switch 50 may be manipulated in such a manner that the user contacts or pushes the control switch 50. In response to the user manipulating the control switch 50, a vibration motor control signal is generated and the generated vibration motor control signal is transferred to the micro-computer 23. The micro-computer 23 may control the operation of the vibration motor 40 in response to the vibration motor control signal.

According to an example embodiment, the vibration frequency of the vibration motor 40 may vary based on whether the vibration motor control signal is generated and a number of generations of the vibration motor control signal.

That is, in response to a number of times that the user operates the control switch 50, the rotary speed or the vibration frequency of the vibration motor 40 may vary.

According to an example embodiment, the vibration frequency of the vibration motor 40 may increase according to an accumulation of a generation of the vibration motor control signal within a preset generation count range of the vibration motor control signal.

For example, if a vibration motor control signal corresponding to a one time is generated in response to the user initially operating the control switch 50, the vibration motor 40 may operate at a preset first vibration frequency. If a vibration motor control signal corresponding to a one time is additionally generated in response to the user controlling the control switch 50 during the operation of the vibration motor 40 at the first vibration frequency, the vibration motor 40 may operate at a second vibration frequency greater than the first vibration frequency. If a vibration motor control signal corresponding to a one time is additionally generated in response to the user controlling the control switch 50 during the operation of the vibration motor 40 at the second vibration frequency, the operation of the vibration motor 40 may be suspended. In this case, the preset generation count range of the vibration motor control signal is two times.

That is, a number of generations of the vibration motor control signal increases within the generation count range of the vibration motor control signal corresponding to two times. Accordingly, the vibration frequency of the vibration motor 40 may change from the first vibration frequency to the second vibration frequency greater than the first vibration frequency.

The preset number of generations of the vibration motor control signal is not limited to two times and may be three times or more. In this example, the vibration frequency of the vibration motor 40 may be set to increase until the number of generations of the vibration motor control signal reaches three times or the preset number of generations.

According to an example embodiment, the vibrator may further include a vibration bushing 35 provided at one end of the vibration tip 31 and accommodated in the housing 10.

The vibration bushing 35 functions to couple with one end of the vibration tip 31 and to decrease a vibration frequency of the vibration tip 31. That is, the vibration bushing 35 decreases the vibration frequency of the vibration tip 31 by adding a mass to the vibration tip 31. If the vibration frequency of the vibration motor 40 is not appropriately controlled, a desired vibration frequency of the vibration tip 31 may be generated by adjusting the mass of the vibration bushing 35.

Meanwhile, the vibration bushing 35 may be disposed to be separate from the vibration motor 40 by a preset distance. Since the vibration bushing 35 and the vibration motor 40 are separate from each other by the preset distance, the vibration generated at the vibration motor 40 may be effectively transferred to the vibration bushing 35 through the housing 10. The vibration tip 31 may vibrate in response to the vibration of the vibration bushing 35.

According to an example embodiment, the vibrator may further include a vibration tip rotation handler 33 provided between the vibration tip 31 and the vibration bushing 35 and configured to rotate the vibration tip 31.

The user may rotate the vibration tip 31 to a desired location through the vibration tip rotation handler 33. In response to rotation of the vibration tip rotation handler 33 through fixable coupling between with the vibration tip 31, the vibration tip 31 also rotates together with the vibration tip rotation handler 33. A location of an end of the vibration tip 31, that is, a location of an end at which the vibration tip 31 is in contact with the composite resin may be changed through the vibration tip rotation handler 33.

The description of the example embodiments is provided as an example only and one of ordinary skill in the art will understand that changes, modifications, alternations, etc., may be easily made thereto without changing the technical spirit or essential features of the disclosure. Accordingly, the example embodiments should be understood as examples only in every aspect and not to be limiting. For example, each component described in a singular form may be distributed and thereby implemented. Likewise, constituent elements described to be distributed may be implemented in a combined form.

Although a few example embodiments have been shown and described, the present disclosure is not limited to the described embodiments. Instead, it would be appreciated by those skilled in the art that changes may be made to these embodiments without departing from the principles and spirit of the disclosure, the scope of which is defined by the claims and their equivalents.

What is claimed is:

1. A vibrator for attaching composite resin to a tooth, the vibrator comprising:
    a housing;
    a vibration motor accommodated in the housing and configured to generate vibration;
    a micro-computer configured to control an operation and a vibration frequency of the vibration motor;
    a vibration tip configured to couple with one side of the housing to be exposed to an outside of the housing, and to transfer the vibration to the composite resin;
    a vibration tip rotation handler coupled with one end of the vibration tip;
    a vibration bushing accommodated in the housing, wherein the vibration bushing is positioned between the vibration tip rotation handler and the vibration motor and configured to decrease a vibration frequency of the vibration tip by adding a mass to the vibration tip; and
    a control switch provided on one side of the housing and configured to generate a vibration motor control signal in response to a user contacting or pushing the control switch,
    wherein the vibration frequency of the vibration motor varies based on a number of times that the vibration motor control signal is generated in response to the user contacting or pushing the control switch, and the vibration motor control signal is generated each time the user contacts or pushes the control switch,
    wherein the vibration frequency of the vibration motor increases according to increase of the number of times that the vibration motor control signal is generated up to a preset generation count number, the preset generation count number being two or more,
    wherein an operation of the vibration motor is suspended in response to a vibration motor control signal being additionally generated according to the user contacting or pushing the control switch one time more than the preset generation count number during the operation of the vibration motor,
    wherein the vibration tip rotation handler is in a shape of a cylinder having an upper surface and a lower surface and extending from the upper surface to the lower surface and configured to be rotated together with the vibration tip according to a user rotation of the vibration tip rotation handler, the upper surface of the vibration tip rotation handler being coupled with the one end of the vibration tip, and wherein the vibration bushing is in a shape of a cylinder having an upper surface and a lower surface and extending from the upper surface of the vibration bushing to the lower surface of the vibration bushing, the upper surface of the vibration bushing faces the lower surface of the vibration tip rotation handler, and the lower surface of the vibration hushing faces the vibration motor and is separate from the vibration motor by a preset distance.

2. The vibrator of claim 1, wherein the vibration motor operates in a first vibration frequency in response to a vibration motor control signal being generated by the control switch according to the user contacting or pushing the control switch a first time, wherein the vibration motor operates in a second vibration frequency in response to a second vibration motor control signal being generated by the control switch according to the user contacting or pushing the control switch a second time during the operation of the vibration motor at the first vibration frequency, the second vibration frequency being greater than the first vibration frequency, wherein the vibration motor operates in a third vibration frequency in response to a third vibration motor control signal being generated by the control switch according to the user contacting or pushing the control switch a third time during the operation of the vibration motor at the second vibration frequency, the third vibration frequency being greater than the second vibration frequency, and wherein an operation of the vibration motor at the third vibration frequency is suspended in response to a fourth vibration motor control signal being generated by the control switch according to the user contacting or pushing the control switch a fourth during the operation of the vibration motor at the third vibration frequency.

\* \* \* \* \*